US006780377B2

(12) United States Patent
Hall et al.

(10) Patent No.: US 6,780,377 B2
(45) Date of Patent: Aug. 24, 2004

(54) ENVIRONMENTAL CONTAINMENT SYSTEM FOR A FLOW CYTOMETER

(75) Inventors: Brian R. Hall, Fort Collins, CO (US); Kristopher S. Buchanan, Fort Collins, CO (US); Benjamin H. Kaanta, Fort Collins, CO (US); Nathan M. Fox, Fort Collins, CO (US)

(73) Assignee: DakoCytomation Denmark A/S, Glostrup (DK)

( * ) Notice: Subject to any disclaimer, the term of this patent is extended or adjusted under 35 U.S.C. 154(b) by 0 days.

(21) Appl. No.: 10/349,710

(22) Filed: Jan. 22, 2003

(65) Prior Publication Data

US 2003/0138967 A1 Jul. 24, 2003

Related U.S. Application Data

(60) Provisional application No. 60/351,148, filed on Jan. 22, 2002.

(51) Int. Cl.[7] .......................... G01N 33/48; B07C 5/00; B01L 3/00
(52) U.S. Cl. .......................... 422/73; 422/99; 422/104; 436/63; 436/174; 436/181; 435/4; 435/29; 209/3.1; 209/576
(58) Field of Search .......................... 436/63, 174, 181; 422/73, 99, 101, 104; 435/4, 29, 30, 287.1, 287.4; 209/3.1, 576

(56) References Cited

U.S. PATENT DOCUMENTS

| 4,230,031 A | 10/1980 | Pedroso et al. ................ 98/115 |
| 4,279,345 A | 7/1981 | Allred ......................... 209/3.2 |
| 5,083,558 A | 1/1992 | Thomas et al. ........ 128/202.12 |
| 5,200,616 A | 4/1993 | Kokawa et al. ............. 250/306 |
| 5,641,457 A | 6/1997 | Vardanega et al. ......... 422/82.1 |
| 5,776,781 A | 7/1998 | Vardanega et al. ............ 436/63 |
| 5,810,988 A | 9/1998 | Smith, Jr. et al. ............ 204/666 |
| 6,149,867 A | 11/2000 | Seidel et al. .................. 422/73 |

FOREIGN PATENT DOCUMENTS

WO    WO 96/17952    6/1996

OTHER PUBLICATIONS

United States Provisional Application No. 60/351,148 filed Jan. 22, 2002 entitled "Adjustably Controllable Environment Containement System for a Flow Cytometer" 17 pages and 4 drawings.

Primary Examiner—Maureen M. Wallenhorst
(74) Attorney, Agent, or Firm—Santangelo Law Offices, P.C.

(57) ABSTRACT

A environmental containment system (16) for a flow cytometer (21) which provides a adjustably controllable environment in which biological particles can be differentiated and droplets separated into collection containers (15).

16 Claims, 4 Drawing Sheets

ENVIRONMENTAL CONTAINMENT SYSTEM FOR A FLOW CYTOMETER

This application claims the benefit of U.S. Provisional Patent Application No. 60/351,148, filed Jan. 22, 2002, hereby incorporated by reference herein.

TECHNICAL FIELD

An environment containment system provides an adjustably controllable environment for cells entrained within the fluid stream generated by a flow cytometer.

BACKGROUND

A flow cytometer or cell sorter is an instrument that physically separates cells according to certain parameters. Many cell sorters use techniques to distinguish subpopulations of cells by employing a unique blend of modern technologies such as fluidics, electric fields, lasers, optics, analog and digital electronics, computers and software.

Referring to FIG. 1, in conventional flow cytometry (1), selected cells can be labeled with fluorescent molecules that bind specifically to the constituent(s) (e.g. using a fluorescently-labelled antibody to a particular surface antigen) to be measured. Certain, desired cells (a subpopulation of cells) may, for example, be fluorescently labeled while other cells in the sample of cells are not fluorescently labeled. In this example, such fluorescently labeled cells may be selectively identified from a heterogeneous cell population.

The cells and a sheath fluid are supplied to the interior volume of a droplet generator (2) from a cell source (3) through an injector tube (4) and a sheath fluid source (5) respectively. The sheath fluid confines, by hydrodynamic focusing, the sample of cells to a central core of the laminar flow that leaves the droplet generator (2) at an orifice (6) as a fluid stream (7). The fluid stream entraining the cells to be sorted, pass such cells, typically one by one, through a beam of excitation light from a light source (8) (which can be a laser or arc lamp), such that each fluorescently labeled cell emits a short flash of fluorescence. The intensity of the fluorescence may be proportional to amount of the fluorescent label on the individual cells. These flashes of fluorescence are collected by a fluorescence collection lens, which focuses the light on a sensitive fluorescence detector (9). The fluorescence detector (9) transforms the flashes of light into electrical pulses, which are measured and recorded by an analysis means (10), which may in part include a computer. Thus, multiple parameters including fluorescence at different wavelengths, as well as size and shape or structure, may be analyzed for each individual cell in the sample of cells.

Once the analysis of an individual cell is made, the flow cytometer (1) has the ability to selectively remove certain cells from the fluid stream (7). Droplets (11) are generated in the fluid stream (7) by the oscillation of the droplet generator (2), which is coupled to an oscillation generator (12) and an oscillation frequency controller (13). A droplet-separation point or break off point, which occurs shortly after the cells leave the droplet generator (2) through orifice (6) become selectively charged by a charging pulse. The charging pulse may be produced by a charging system control logic that is coupled to receive signals from the analysis means (10). The charging system control logic analyzes signals from the analysis means (10) and determines whether the cell is to become a selected cell and, if so, applies the charging pulse to the conductive fluid carrying the cells just before the droplet carrying the cell breaks off from the fluid stream (7). The droplet (11) carrying the selected cell separates as a charged droplet from the fluid stream (7) and falls, under the force of gravity, through a constant electric field produced by the deflecting system (14). If the cell is not a selected cell, then charging system control logic will not apply the charging pulse, and the droplet (11) containing this cell will separate from the fluid steam (7) as an uncharged droplet and will fall through the electric field largely unaffected by this field. Typically, one droplet (11) will contain only one cell so that the selective charging of a droplet will select only one cell.

The deflecting system (14) alters the trajectory in which the charged droplets (11) are traveling such that the charged droplets are physically separated from the uncharged droplets according to the value of the parameters analyzed or measured by the analysis means (10). After passing through the deflecting system (14), the droplets are collected in a cell collector (15) that may have several different collection receptacles or containers. Additional background information may be obtained by referring to Flow Cytometry and Sorting, Second Edition by Myron R. Melamed, Tore Lindmo, Mortimer Mendelsohn, published by Wiley-Liss New York, N.Y., 1990. Also see, for example, U.S. Pat. Nos. 5,150,313, and 3,560,754, each hereby incorporated by reference.

Although technology has led the way for a new generation of cell sorters that are simpler to operate and maintain, and significantly less expensive both to purchase and to operate, the inability to analyze, measure, or sort cells in an adjustably controllable environment significantly limits the types of applications to which flow cytometers or cell sorters may be used. And while various solutions have been suggested or proposed such as those disclosed by U.S. Pat. Nos. 5,776,781; 5,641,457; 5,083,558; and 5,200,616, each hereby incorporated by reference, significant problems remain unresolved.

A significant problem with conventional flow cytometry technology may be that aerosols, containing hazardous materials, are generated around the nozzle during and after the sorting of the cells. One aspect of this problem may be that these hazardous, dangerous, or undesirable aerosols or contaminants can be adsorbed on the surfaces of the flow cytometer resulting in premature wear. Another aspect of this problem may be that these undesirable aerosols may be inhaled or absorbed through the skin of person(s) in proximity to the flow cytometer. Moreover, these aerosols may, with respect to samples or other chemicals, represent an undesired contaminant.

Another significant problem with conventional flow cytometry technology may be that the cells, biological materials associated with the cells, or other materials being analyzed with the flow cytometer may be susceptible to contamination, modification, molecular rearrangement, or the like, by exposure to the open air; constituents of the open air; or particles, chemicals, other biological materials, such as bacteria, viruses, pollen, microscopic flora or fauna, or other pathogens that can be carried by the open air.

A controlled sterile flow cytometer environment, for example, that prevents cells from being contaminated and also maintains their viability, may allow the sorted cells to be used for further processes such as genetic modification of the sorted cells themselves, isolation or preservation of the cells in a frozen state, or culturing of the isolated cells in conventional tissue culture media, administering the isolated cells to a patient, or various permutations and combinations of these or other processes. An example of such a combination might involve removing a sample of blood from a patient, labeling certain cells (e.g. pluripotent hematopoietic stem cells) with fluorescently labeled antibodies and isolating these cells using the sterile cell sorter by observing and measuring the emitted excitation wavelengths from these fluorescently labeled antibodies, culturing these isolated certain cells and genetically modifying them (e.g. using recombinant DNA technology) to provide genetically modified cells, and culturing these cells in a tissue culture media and injecting them back into the patient to provide a cure or remedy for a disease.

Another significant problem with conventional flow cytometer technology may be that protective enclosures presently manufactured such as those disclosed by U.S. Pat. Nos. 4,063,495; 4,045,192; 3,462,920; and 3,511,162, each hereby incorporated by reference, are arranged to substantially enclose the protected area and do not permit a great deal of access for manual operations, or other features that are useful with respect to flow cytometry procedures.

Another significant problem with conventional flow cytometer technology may be that the protective enclosures do not provide a disposable liner for the protective enclosure. As such, the protective enclosure itself can become contaminated with the cells, biological materials, or aerosoled chemicals, contaminants, or the like, which can then contaminate samples subsequently analyzed.

As to these problems associated with conventional flow cytometry technology, the instant invention addresses each with a practical solution.

SUMMARY OF THE INVENTION

Accordingly, a broad object of embodiments of the invention can be to provide an adjustably controllable environment containment system for a flow cytometer to protect both the particles being processed by the flow cytometer from contamination by both biological and non-biological materials and to protect persons using the flow cytometer from being exposed to the particles being processed and the chemistry utilized in the processing of such particles.

A significant object of embodiments of the invention can be to provide a environmental containment element (also referred to as an enclosure) that can separate the adjustably controlled environment within containment element from the undesired environment outside the containment element.

Another significant object of certain embodiments of the invention can be to provide an environmental containment element having a configuration such that upon introduction of a desired mixture of gases into such enclosure the fluid stream along the trajectory between orifice of the droplet generator to the collection container is maintained within such mixture of gases.

Another significant object of embodiments of the invention can be to protect the particles, or molecules embedded in the surface of such particles, being processed by a flow cytometer from reacting with the environment to produce unwanted modification(s) or molecular rearrangement(s); or being contaminated with microflora or microfauna, such as bacteria, viruses, pollen, or other biological pathogens, or the like.

Another significant object of embodiments of the invention can be to process particles (such as cells) in an environment that allows the products of the process to be used in further processes, such as genetic modification of the particles or cells themselves; allows isolation or preservation of the cells in a frozen state; culturing of the cells in tissue culture methods; or administering the processed or isolated cells, directly or after further processing into animal, including human, patients to provide a cure or remedy for disease.

Another significant object of embodiments of the invention can be to provide a method and devices for effectively cleaning the surface areas that surround the adjustably controlled environment.

Another significant object of embodiments of the invention can be to provide a flow cytometer that measures, but does not sort, cells. The ability to measure cells in a sterile environment is crucial when handling biological cells that are intended to be used for further cultivation or other processes requiring sterility.

Another significant object of embodiments of the invention can be to provide an enclosed environment that can be sterilized and furthermore, maintain its sterility during the actual measuring or sorting of cells. Although the present invention includes several subsystems, it is essential to have only certain subsystems located within the enclosed environment, but when these subsystems work in conjunction with those subsystems located outside the enclosed environment, the sterility of the enclosed environment can still be maintained.

Another significant object of embodiments of the invention can be to provide an enclosed environment that is functional. In other words, in addition to encompassing the subsystems that must be kept sterile, the enclosed environment must provide an environment in which the user, located outside the sterile environment can properly operate the cell sorter within the enclosed environment. The enclosed environment may include adequate work space for the operator, the proper equipment and tools as well as a storage place for them when not in use, a transfer port for transferring items in and out of the enclosed environment without breaking the sterility of the isolation chamber, adequate safety mechanisms to prevent the operator from being injured, and an interface for the operator to conveniently and comfortably work inside the sterile environment while located outside the enclosed environment.

Another significant object of embodiments of the invention can be to provide a method for sterilizing the enclosed environment before measuring and sorting the cells, and for maintaining a sterile air pressure within the enclosed environment during the measuring or sorting of the cells. Sterilization may be repeated at the end of measuring or sorting in order to decontaminate the enclosure when measuring or sorting cells or samples which may be infected (e.g. HIV infected blood). This sterilization after measuring or sorting protects the user of the cell sorter form unhealthy contaminants.

Another significant object of embodiments of the invention can be to provide a sterilization system to ensure that during the measuring and sorting of the cells, the isolation chamber is maintained at a pressure above atmospheric pressure which is used to maintain the sterility of the isolation chamber.

Naturally, further objects of the invention are disclosed through the description and by the drawings.

DETAILED DESCRIPTION OF THE PREFERRED EMBODIMENTS

An adjustably controllable environment in which biological cells, or other particles, can be transferred, differentiated, sorted, or otherwise manipulated while the fluid stream entraining such particles is maintained in a desired mixture of gases.

Figure 1:
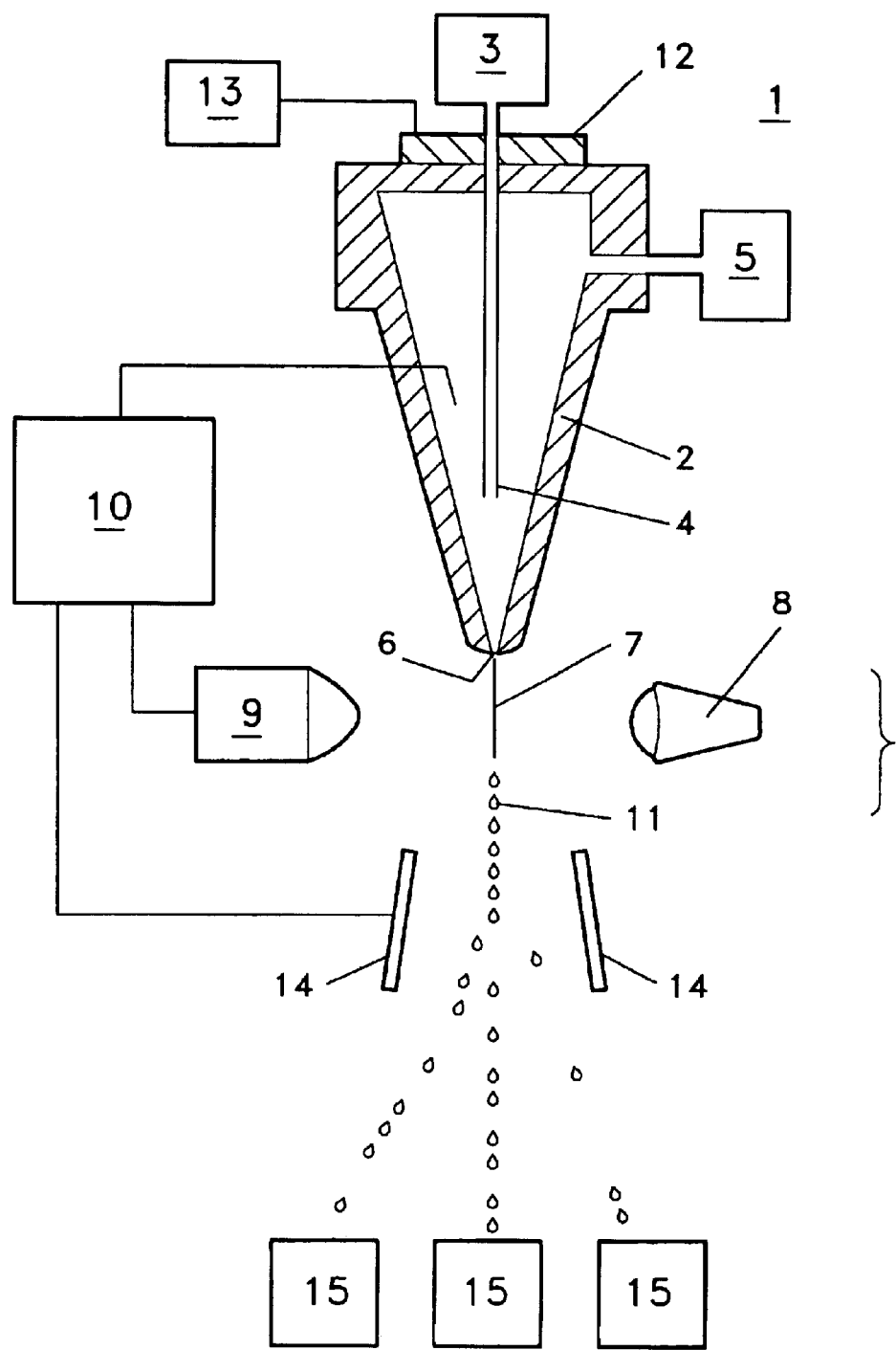
FIG. 1 is diagrammatic representation of an embodiment of conventional flow cytometer.
Figure 2:
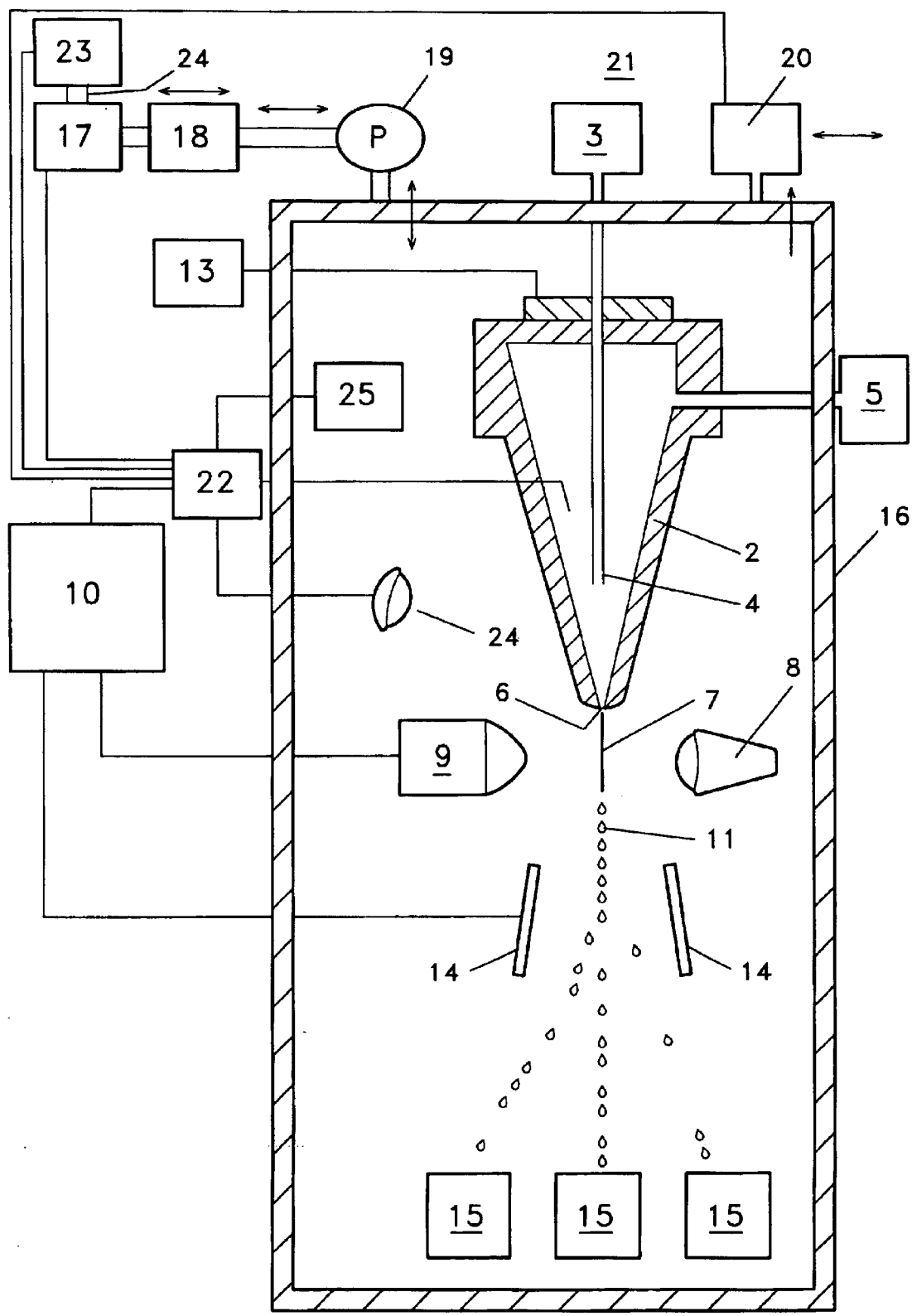
FIG. 2 is a diagrammatic representation of an embodiment of the adjustably controllable environment containment system invention.

Now referring primarily to FIG. 2, embodiments of the invention can comprise flow cytometer system(s) (21) that further include an adjustably controllable environment containment system (16). Cells, biological materials, biological particles, non-biological particles or the like can be analyzed, measured, or physically separated within a desired mixture of gases while many instrument subsystems may be located outside of the adjustably controlled environment.

For example, the subsystems which are involved in making the actual analysis of the cells, biological materials, particles, or the like, including the analysis means (10) which allows for discrimination, differentiation or measurement of the cells; or the environment controlling means (22) which controls the operation of subsystems; can be located outside of the adjustably controllable environment containment system (16). Those external subsystems can be connected to the subsystems located within the environment containment system (16) by various electrical or mechanical conduits which pass through openings or apertures in the adjustably controllable environment containment system (16).

For example, with respect to some embodiments of the invention, the excitation source (8) can be a subsystem located inside the environmental containment system (16) but could also be located outside the environmental containment system (16). The detector system (9), including optics, detector(s), and electronics, can also a subsystem of the present invention located either inside or outside the environmental containment system (16), as shown in FIG. 2. With respect to the specific embodiment of the invention shown in FIG. 3 (discussed in detail below) the flow cytometer nozzle or droplet generator (2) can be positioned to be entirely or partially outside the actual enclosure while the collection container(s)(15) can be located inside the environmental containment enclosure (16).

Embodiments of the invention, can maintain a sterile or substantially sterile environment within the environmental containment system (16) prior to operation of the flow cytometer or during the period in which cells, biological materials, or other particles are transferred, analyzed, sorted, measured, or otherwise manipulated. To maintain the sterility of the environmental containment system, a pressure differential generator (19) located outside the environmental containment system (16), can inject or introduce air (or any mixture of partial pressures of gases desired) into the environmental containment system (16) through conduits that communicate from the interior to the exterior of the environmental containment system (16). Air or other mixture of gases introduced into the environmental containment system (16) can be prefiltered or scrubbed by a filter system(s) (17) or a gas scrubber system(s) (18). Naturally, any kind or number of gas scrubbers or filters can be utilized in line or in parallel to condition or adjust the partial pressures of the mixture of gases or remove biological particles (such as pathogens, bacteria, viruses, or the like), organic particulates, or inorganic particulates, delivered to the environmental containment system (16). The sum of the partial pressures of the mixture of gases within the enclosure (26) remains positive with respect to the sum of the partial pressures of gases outside the enclosure (26).

Additionally, gases, sterilants (such as formaldehyde or chlorine gases), other compounds, or the like (23) not typically present in air can be introduced into the gas stream delivered to the environmental containment system (16), if desired. Gas may be introduced into a conduit (24) from an external pressurized gas source (not shown) which communicates with the air scrubber system or the air filter system, or both. Additional gas connections can optionally provide for admitting gas(es) from an additional gas source(s). The flow of gas can be further controlled by a valve system (20) that can be responsive to environment controlling means (22) so that air pressure and direction are maintained as desired. Alternately, automatic, pressure-sensitive inlet and outlet valves can be provided to maintain a constant pressure inside the environmental containment system (16).

In alternate embodiments of the invention, air or other mixture of gases can be withdrawn from the environmental containment system (16) and the gas scrubber or filter systems (17)(18) can be used to remove particulate, contaminants, pathogens, or chemicals from the gas stream prior to being introduced in the atmosphere surrounding the environmental containment system (16).

Naturally, embodiments of the invention can further include the combination of introducing or withdrawing a desired mixture of gases or air into or from the environmental containment system (16) which can further be located, along with the desired subsystems, within a clean air hood, fume hood, or microbiological containment hood, or the like.

In other embodiments of the invention, a short wavelength ultraviolet radiation source (24) can bathe the interior of the environmental containment in order to sterilize the interior; in this embodiment, the ultraviolet light sources (24) can be coupled to the interior of the environmental containment system (16).

Embodiments of the invention can further provide a temperature control means (25) for maintaining a constant temperature of the gas contained within the environmental containment system (16). A temperature control module that includes a temperature sensor for detecting the temperature inside environmental containment system (16) can be further included. Responsive to the temperature sensor can be a heating unit or cooling unit(s) which warms the circulating gas.

Figure 3:
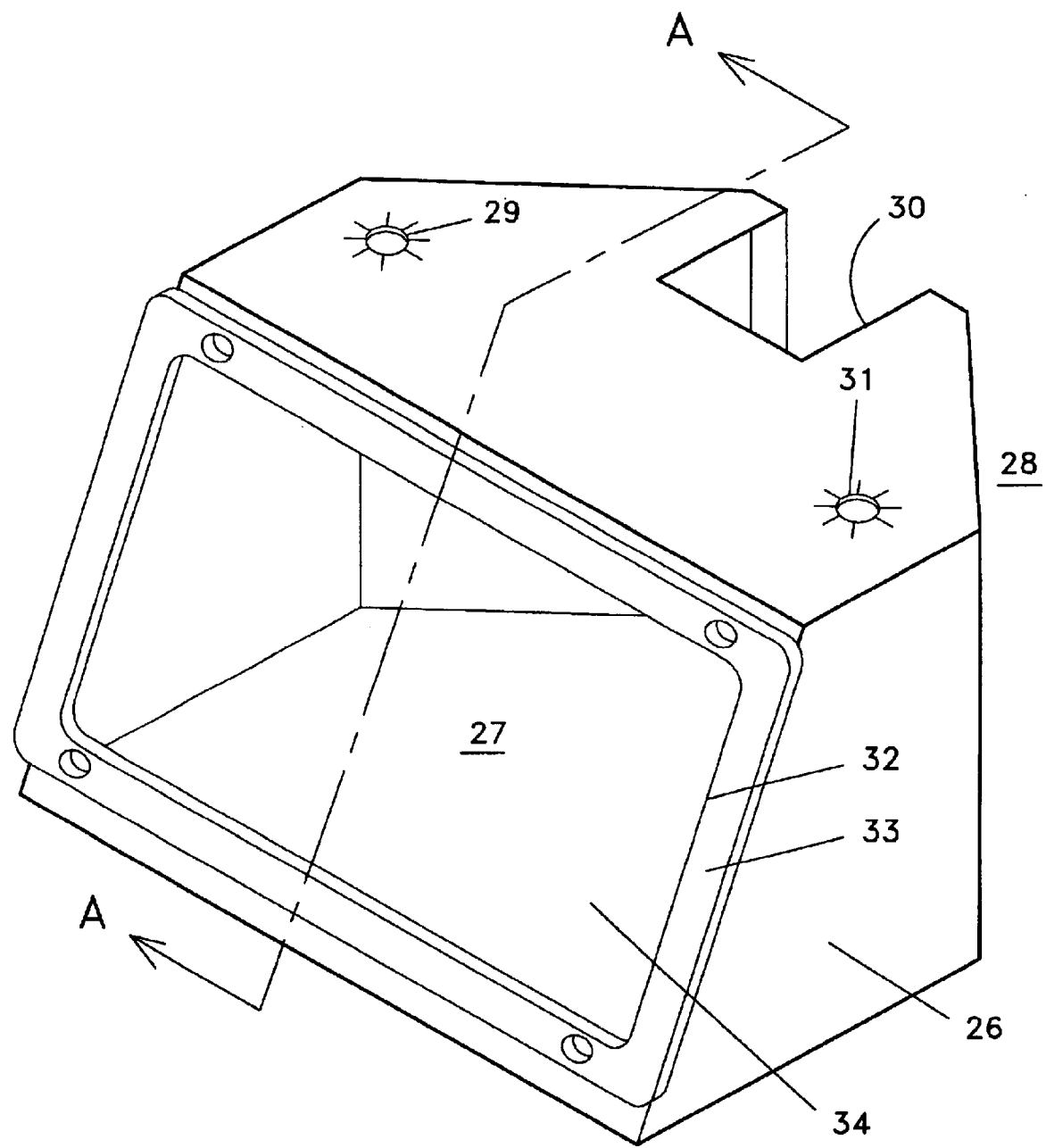
FIG. 3 is an isometric view of one of a variety of embodiments of an environment containment element.

Now referring primarily to FIG. 3, certain embodiments of the environmental containment system can comprise or include an enclosure (26) configured to separate an adjustably controllable environment (27) from the external environment (28). While the embodiment of the enclosure (26) shown in FIG. 3 has a configuration to provide an adjustably controllable environment (27) for a Cytomation MoFlo® flow cytometer, it should be understood that the enclosure (26) shown is not intended to limit the use of the invention solely to Cytomation MoFlo® flow cytometer(s). The varied and numerous embodiments of the invention can provide an enclosure (26) configured for use with other models of flow cytometers produced by Cytomation, Inc., Bectin Dickinson, Inc., or other manufacturers.

The enclosure (26) can be made of plastic, metal, or other material non-reactive with the types of chemistry, or the types of particles, used with a flow cytometer (or other instrument that may similarly utilize the invention). The material used in the production of the enclosure (26) can be configured using a single step or configured using multiple steps of injection molding, vacuum forming, pressing, or other type of conventional fabrication using a single piece of material or separate pieces of material which are bonded or fastened together, or combinations or permutations thereof.

Certain embodiments of the invention can further comprise a gas inlet element (29) through which selected gases, such as air, compressed gases, or any predetermined mixture or partial pressures of gases, which may further include any sterilants, or other compounds, as desired, can be introduced into the enclosure (26). A gas outlet element (31) can be further added in some embodiments to relieve or balance pressure of the mixture gases in the enclosure (26). An aperture element (30) can be provided to provide an unimpeded flow path for the liquid stream between the orifice (6) of the flow cytometer nozzle and the collection container (15) located within the enclosure (26)(individual collection tubes, multiple welled collection trays, or the like may be used). The total pressure of the partial pressures of gases introduced into the enclosure can be adjusted to establish a flow of such partial pressure of gases within the enclosure (26) and through the aperture element (30) to the external environment (28). The droplet generator or nozzle (2) can be aligned with the aperture element (30) such that one or more fluid stream or droplet trajectories are established between the orifice (6) and the collection container(s)(15) within the enclosure (26) which are entirely or partially within or enveloped by the mixture of gases flowing from the aperture element (30).

Alignment of the flow cytometer nozzle (2) with the aperture element (30) positions the droplet generator (2) at a location outside of, or partially or entirely within, the enclosure (26) depending on the configuration of the aperture element (30) and the configuration of the droplet generator (2) and associated subsystems (8)(9)(24)(14). Naturally, depending on the flow cytometry subsystems that are to be held within the adjustably controllable environment (27), the enclosure (26), the access element (30), the gas inlet (29), or the gas outlet (31) can be configured or positioned differently to provide accommodation of such subsystems.

Certain embodiments of the enclosure (26) can further provide an access aperture (32) which allows manipulation, by hand or hand held instruments, of collection containers (15) or other objects within the enclosure. An access aperture frame (33) can be connected to the enclosure (26) to stiffen or strengthen the terminal edges of the access aperture (30), or to provide for attachment of a screen (34) which may be of sufficient transparency to view the space inside the enclosure (26). The screen (34) can be movably coupled to the containment element (26) or the access aperture frame (33). Various embodiments of the movably coupled screen (34) can include for example a screen that can be completely removed from the containment element as a discrete element, or so that it is rotationally coupled (with hinges, pivots, or the like), or so that it is slideably coupled to the viewing aperture, or various permutations and combinations thereof. Alternately, the enclosure (26) can be fabricated to include an integral section or portion having sufficient transparency such that the space within the enclosure can be viewed.

Figure 4:
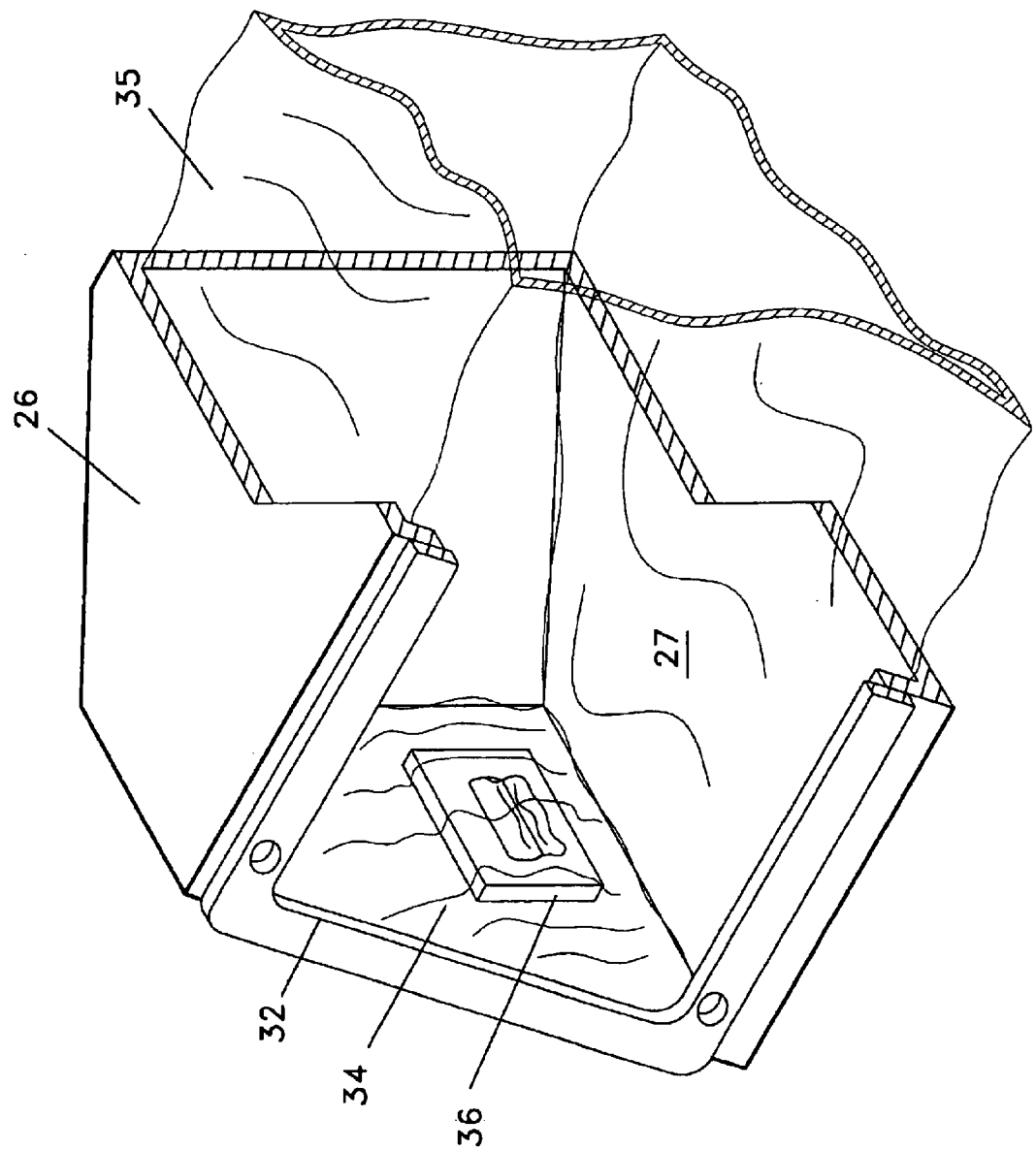
FIG. 4 is a cross section through FIG. 3 showing an embodiment of a liner element to be used with certain embodiments of the environment containment element.

Now referring primarily to FIG. 4, certain embodiments of the enclosure (26) can further comprise a liner element (35). The liner element can be made of a thin membrane or layer of material that is resistant to the chemistry used with the flow cytometer or to the particles, cells, other biological particles, or non-biological particles processed by the instrument, or both. The liner element (35) can be installed so that one surface of the liner element substantially conforms to the inside surface of the enclosure (26). The liner element (35) can be reduced in volume, such as by folding, or vacuum packaging or a combination thereof, or a plurality of liner elements (35) can be packaged together in a reduce volume manner (36). In certain embodiments, a plurality of liner elements can be packaged and installed in the adjustably controllable environment (27) so that when one liner element (35) is disposed of a sterile replacement can be available in the adjustably controllable environment (27).

To initially fill the enclosure (26) with air or the desired mixture of gases, the desired mixture of gases at desired partial pressures gases are transferred through the desired particle filter (17) or gas scrubber (18) to the gas inlet element (29). When the enclosure (26) is filled, excess gas can be expelled from the adjustably controlled environment (27) through the gas outlet element (31) or aperture element (30). The adjustably controlled environment can be filled and replaced several times to assure that the final atmosphere inside the apparatus is as desired. Introduction of the mixture of gases into the enclosure (26) is adjusted to maintain a flow within the enclosure as desired. As to certain embodiments of the invention sufficient flow within the enclosure (26) and through the aperture element (31) can be maintained by introducing between 1 cubic foot and 50 cubic feet of the desired mixture of gases per minute. Aerobic mixture of gases can be adjusted to suit a particular species of aerobic organism, if desired.

Embodiments of the invention can further provide an adjustably controlled anaerobic environment, for example, the adjustably controlled environment (27) may be filled and replaced several times with dry nitrogen and filled the final time with the anaerobic mixture of gases desired. Anaerobic gases can include nitrogen, hydrogen, and carbon dioxide in such a ratio that the mixture is not explosive if exposed to air and heat. The anaerobic mixture of gases may be varied to suit the particular specimens being separated. One mixture, suitable for many anaerobic species, is 7 percent H, 5 percent $CO_2$, and 88 percent N.

If anaerobic conditions are to be maintained it is also convenient to provide an oxygen detection means, such as an indicator dye within the adjustably controlled environment (27), to alert the operator if the atmosphere inside the enclosure (26) becomes contaminated with oxygen. Naturally, the example of an anaerobic environment is one of various adjustably controlled environments (anaerobic or aerobic) that can be maintained, as desired, and it is understood that this example is not limiting with respect to the various embodiments of adjustably controlled environments that can be maintained within the enclosure (26).

Another adjustably controlled environment (27) that can be maintained during flow separation of cells comprises a substantially particle free environment. A particle free gas (or any mixture of particle free partial pressures of gases) can be introduced into the enclosure (26) at sufficient volume, flow rate, velocity, combination thereof, such that the sum of the partial pressures of the mixture of gases within the enclosure (26) remains positive with respect to the sum of the partial pressures of gases outside the enclosure (26).

The particle free gas injected within the enclosure (26) can be generated by passing the desired mixture of gases through a filter, such as a HEPA filter prior to its introduction into the enclosure (26). In this manner all of the gas within the enclosure (26) may be maintained substantially particle free and a clean environment can be achieved or maintained.

As can be easily understood from the foregoing, the basic concepts of the present invention may be embodied in a variety of ways. It involves methods for adjustably controlling the environment surrounding the process(es) of fluid stream generation, droplet formation, droplet separation, or droplet collection in the context of flow cytometry as well as devices to accomplish controlling the environment surrounding droplet formation, droplet sorting, or droplet collection. In this application, methods of adjustably controlling the environment certain flow cytometer processes is disclosed as part of the results shown to be achieved by the various devices described and as steps that are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in a full patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent continuing application.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element, which causes that action. Similarly, each physical element disclosed should be understood to encompass a disclosure of the action that physical element facilitates. Regarding this last aspect, as but one example, the disclosure of a "sorter" should be understood to encompass disclosure of the act of "sorting"—whether explicitly discussed or not—and, conversely, were there effectively disclosure of the act of "sorting", such a disclosure should be understood to encompass disclosure of a "sorter" and even a "means for sorting" Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference.

Thus, the applicant(s) should be understood to claim at least: i) an adjustably controllable environment containment system as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and apparatuses substantially as described hereinbefore and with reference to any of the accompanying examples, and x) the various combinations and permutations of each of the elements disclosed.

Further, if or when used, the use of the transitional phrase "comprising: is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

We claim:

1. An enclosed environment, comprising:
   a. a conduit having an orifice element;
   b. a liquid flow in said conduit;
   c. a liquid stream generated at said orifice element;
   d. a container to collect said liquid stream;
   e. an enclosure having an aperture element, wherein said container has a location in said enclosure, and wherein said liquid stream has a trajectory from said orifice element to said container in said enclosure; and
   f. a mixture of gases introduced into said enclosure which flow through said aperture element, wherein said flow through said aperture element maintains said liquid stream having said trajectory from said orifice element to said container within said mixture of gases.
   wherein said mixture of gases introduced into said enclosure has a percent ratio different than percent ratio of atmospheric gases.

2. An enclosed environment, comprising:
a. a conduit having an orifice element;
b. a liquid flow in said conduit;
c. a liquid stream generated at said orifice element;
d. a container to collect said liquid stream;
e. an enclosure having an aperture element, wherein said container has a location in said enclosure, and wherein said liquid stream has a trajectory from said orifice element to said container in said enclosure; and
f. a mixture of gases introduced into said enclosure which flow through said aperture element, wherein said flow through said aperture element maintains said liquid stream having said trajectory from said orifice element to said container within said mixture of gases,
wherein said mixture of gases introduced into said enclosure comprises mixture of gases selected to maintain a species of anaerobic organism.

3. An enclosed environment as described in claim 2, wherein said mixture of gases introduced into said enclosure comprises about seven percent hydrogen, about five percent carbon dioxide, and about 88 percent nitrogen.

4. An enclosed environment as described in claim 3, further comprising an oxygen detector within said enclosure and responsive to said mixture of gases introduced into said enclosure.

5. An enclosed environment as described in claim 4, further comprising a signal generator responsive to said oxygen detector.

6. An enclosed environment, comprising:
a. a conduit having an orifice element;
b. a liquid flow in said conduit;
c. a liquid stream generated at said orifice element;
d. a container to collect said liquid stream;
e. an enclosure having an aperture element, wherein said container has a location in said enclosure, and wherein said liquid stream has a trajectory from said orifice element to said container in said enclosure; and
f. a mixture of gases, including a sterilant, introduced into said enclosure which flow through said aperture element, wherein said flow through said aperture element maintains said liquid stream having said trajectory from said orifice element to said container within said mixture of gases,
wherein said mixture of gases introduced into said enclosure comprises a mixture of gases selected to maintain a species of aerobic organism.

7. An enclosed environment, comprising:
a. a conduit having an orifice element;
b. a liquid flow in said conduit;
c. a liquid stream generated at said orifice element;
d. a container to collect said liquid stream;
e. an enclosure having an aperture element, wherein said container has a location in said enclosure, and wherein said liquid stream has a trajectory from said orifice element to said container in said enclosure;
f. a mixture of gases introduced into said enclosure which flow through said aperture element, wherein said flow through said aperture element maintains said liquid stream having said trajectory from said orifice element to said container within said mixture of gases; and
g. a sterilant introduced into said enclosure with said mixture of gases,
where said sterilant comprises formaldehyde gas.

8. An enclosed environment, comprising:
a. a conduit having an orifice element;
b. a liquid flow in said conduit;
c. a liquid stream generated at said orifice element;
d. a container to collect said liquid stream;
e. an enclosure having an aperture element, wherein said container has a location in said enclosure, and wherein said liquid stream has a trajectory from said orifice element to said container in said enclosure;
f. a mixture of gases introduced into said enclosure which flow through said aperture element, wherein said flow through said aperture element maintains said liquid stream having said trajectory from said orifice element to said container within said mixture of gases; and
g. a sterilant introduced into said enclosure with said mixture of gases,
wherein said sterilant comprises chlorine gas.

9. An enclosed environment comprising:
a. a conduit having an orifice element;
b. a liquid flow in said conduit;
c. a liquid stream generated at said orifice element;
d. a container to collect said liquid stream;
e. an enclosure having an aperture element, wherein said container has a location in said enclosure, and wherein said liquid stream has a trajectory from said orifice element to said container in said enclosure;
f. a mixture of gases introduced into said enclosure which flow through said aperture element, wherein said flow through said aperture element maintains said liquid stream having said trajectory from said orifice element to said container within said mixture of gases; and
g. a gas temperature adjustment system positioned to control the temperature of said mixture of gases within said enclosure.

10. An enclosed environment comprising:
a. a conduit having an orifice element;
b. a liquid flow in said conduit;
c. a liquid stream generated at said orifice element;
d. a container to collect said liquid stream;
e. an enclosure having an aperture element, wherein said container has a location in said enclosure, and wherein said liquid stream has a trajectory from said orifice element to said container in said enclosure; and
f. a mixture of gases, including a sterilant, introduced into said enclosure which flow through said aperture element, wherein said flow through said aperture element maintains said liquid stream having said trajectory from said orifice element to said container within said mixture of gases,
wherein a portion of said enclosure is transparent.

11. An enclosed environment comprising:
a. a conduit having an orifice element;
b. a liquid flow in said conduit;
c. a liquid stream generated at said orifice element;
d. a container to collect said liquid stream;
e. an enclosure having an aperture element, wherein said container has a location in said enclosure, and wherein said liquid stream has a trajectory from said orifice element to said container in said enclosure;
f. a mixture of gases introduced into said enclosure which flow through said aperture element, wherein said flow through said aperture element maintains said liquid stream having said trajectory from said orifice element to said container within said mixture of gases; and g) an access element coupled to said enclosure, wherein said access element comprises a removable transparent screen.

12. An enclosed environment comprising:
a. a conduit having an orifice element;
b. a liquid flow in said conduit;
c. a liquid stream generated at said orifice element;
d. a container to collect said liquid stream;
e. an enclosure having an aperture element, wherein said container has a location in said enclosure, and wherein said liquid stream has a trajectory from said orifice element to said container in said enclosure;
f. a mixture of gases introduced into said enclosure which flow through said aperture element, wherein said flow through said aperture element maintains said liquid stream having said trajectory from said orifice element to said container within said mixture of gases, and
g. a flexible transparent liner disposed between said mixture of gases introduced into said enclosure and said enclosure.

13. An enclosed environment as described in claim 12, further comprising a liner dispenser installed in said enclosure and which dispenses said flexible transparent liner.

14. An enclosed environment comprising:
a. a conduit having an orifice element;
b. a liquid flow in said conduit;
c. a liquid stream generated at said orifice element;
d. a container to collect said liquid stream;
e. an enclosure having an aperture element, wherein said container has a location in said enclosure, and wherein said liquid stream has a trajectory from said orifice element to said container in said enclosure;
f. a mixture of gases, including a sterilant, introduced into said enclosure which flow through said aperture element, wherein said flow through said aperture element maintains said liquid stream having said trajectory from said orifice element to said container within said mixture of gases;
g. an oscillator which generates oscillations to which said liquid stream responds;
h. droplets that break off from said liquid stream, and
i. particles entrained in said liquid stream,
where said container to collect said liquid stream comprises a droplet collector,
wherein said conduit having an orifice element comprises a flow cytometer nozzle,
wherein a portion of said droplets that break off from said liquid stream contain one of said particles, and
wherein said particles comprise non-biological particles.

15. An enclosed environment comprising:
a. a conduit having an orifice element;
b. a liquid flow in said conduit;
c. a liquid stream generated at said orifice element;
d. a container to collect said liquid stream;
e. an enclosure having an aperture element, wherein said container has a location in said enclosure, and wherein said liquid stream has a trajectory from said orifice element to said container in said enclosure;
f. a mixture of gases introduced into said enclosure which flow through said aperture element, wherein said flow through said aperture element maintains said liquid stream having said trajectory from said orifice element to said container within said mixture of gases;
g. an oscillator which generates oscillations to which said liquid stream responds;
h. droplets that break off from said liquid stream, and
i. particles entrained in said liquid stream,
where said container to collect said liquid stream comprises a droplet collector,
wherein said conduit having an orifice element comprises a flow cytometer nozzle,
wherein a portion of said droplets that break off from said liquid stream contain one of said particles,
wherein said particles comprise biological particles, and
wherein said biological particles comprise anaerobic organisms.

16. An enclosed environment comprising:
a. a conduit having an orifice element;
b. a liquid flow in said conduit;
c. a liquid stream generated at said orifice element;
d. a container to collect said liquid stream;
e. an enclosure having an aperture element, wherein said container has a location in said enclosure, and wherein said liquid stream has a trajectory from said orifice element to said container in said enclosure;
f. a mixture of gases, including a sterilant, introduced into said enclosure which flow through said aperture element, wherein said flow through said aperture element maintains said liquid stream having said trajectory from said orifice element to said container within said mixture of gases;
g. an oscillator which generates oscillations to which said liquid stream responds;
h. droplets that break off from said liquid stream, and
i. particles entrained in said liquid stream,
where said container to collect said liquid stream comprises a droplet collector,
wherein said conduit having an orifice element comprises a flow cytometer nozzle,
wherein a portion of said droplets that break off from said liquid stream contain one of said particles,
wherein said particles comprise biological particles, and
wherein said biological particles comprise aerobic organisms.

* * * * *